United States Patent

Miyajima et al.

[11] Patent Number: 5,304,380
[45] Date of Patent: Apr. 19, 1994

[54] GLUCOSAMINE DERIVATIVE AND LIPOSOME CONTAINING THE SAME AS MEMBRANE CONSTITUENT

[75] Inventors: Koichiro Miyajima; Kaoru Fuji, both of Uji, Japan

[73] Assignee: Japan Tobacco Inc., Tokyo, Japan

[21] Appl. No.: 895,444

[22] Filed: Jun. 8, 1992

Related U.S. Application Data

[63] Continuation of Ser. No. 720,479, Jul. 9, 1991, abandoned.

[30] Foreign Application Priority Data

Nov. 9, 1989 [JP] Japan .................................. 1-289933
Oct. 22, 1990 [JP] Japan .................................. 2-281988
Oct. 22, 1990 [JP] Japan .................................. 2-281989

[51] Int. Cl.$^5$ .................. B01F 17/56; A61K 9/127; B01J 13/02; C07H 13/06; C07H 15/104
[52] U.S. Cl. ............................ 424/450; 536/4.1; 536/18.7
[58] Field of Search ................ 424/450; 536/4.1, 18.7

[56] References Cited

U.S. PATENT DOCUMENTS

| | | | |
|---|---|---|---|
| 4,322,523 | 3/1982 | Wagner | 536/4.1 |
| 4,323,561 | 4/1982 | Nowotny | 536/53 |
| 4,485,054 | 11/1984 | Mezei et al. | 424/450 |
| 4,818,816 | 4/1989 | Petitou et al. | 536/55.2 |
| 4,883,665 | 11/1989 | Miyazima et al. | 424/450 |
| 5,032,505 | 7/1991 | Pierce et al. | 536/4.1 |
| 5,041,427 | 8/1991 | Takayama et al. | 536/18.7 |
| 5,059,685 | 10/1991 | Conti | 536/18.7 |

FOREIGN PATENT DOCUMENTS

9171710 2/1986 European Pat. Off. .

(List continued on next page.)

OTHER PUBLICATIONS

"Eur. J. Biochem. 47" (1974) pp. 173-179.

(List continued on next page.)

*Primary Examiner*—Ronald W. Griffin
*Attorney, Agent, or Firm*—Birch, Stewart, Kolasch & Birch

[57] ABSTRACT

Disclosed are a glucosamine derivative represented by the following formula [I] or a pharmacologically acceptable salt thereof, and a liposome containing the glucosamine derivative as a membrane constituting component:

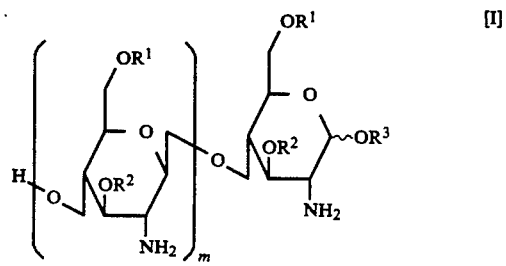

wherein $R^1$, $R^2$, $R^3$, and m represent the following $R^1$ and $R^2$;
    a hydrogen atom or a —CO(CH$_2$)$_n$CH$_3$ group, n representing an integer from 10 to 22 and $R^1$ and $R^2$ being not simultaneously hydrogen atoms $R^3$;
    a hydrogen atom or a lower alkyl group, and m;
    an integer from 0 to 3.

9 Claims, No Drawings

FOREIGN PATENT DOCUMENTS

| | | |
|---|---|---|
| 0192296 | 8/1986 | European Pat. Off. . |
| 0333490 | 9/1989 | European Pat. Off. . |
| 0335597 | 10/1989 | European Pat. Off. . |
| 0346472 | 12/1989 | European Pat. Off. . |
| 60-7934 | 1/1985 | Japan . |
| 61-50912 | 3/1986 | Japan . |
| 61-227586 | 10/1986 | Japan . |
| 62-36306 | 2/1987 | Japan . |
| 63-77824 | 4/1988 | Japan . |
| 63-211222 | 9/1988 | Japan . |
| 1-175944 | 7/1989 | Japan . |
| 1-238537 | 9/1989 | Japan . |
| 1-246225 | 10/1989 | Japan . |

OTHER PUBLICATIONS

"Journal of the Neurological Sciences" 1977, 31: pp. 173–179.

"Chemistry Letters" Cmltag (11), 1980 pp. 1373–1376.

"Drug Delivery System" vol. 2, No. 1, 1987, pp. 48–51.

Katsura et al., 111 Chemical Abstracts No. 45278y (1988).

Ekimoto et al., 112 Chemical Abstracts No. 165001v (1989).

Anderson, et al., Bacterial Lipopolysaccharides, 1983, pp. 255–275.

Chemical Abstracts, vol. 100, No. 13, Mar. 26, 1984, p. 693, 103782u, Chem. Abstr. Eleventh Collective Index, vols. 96–105, 1982–1986, Formula C38H73NO7; Formula C73H117N08.

Chemical Abstracts, vol. 107, No. 5, Aug. 3, 1987, p. 402, 46060a, and Chemical Formula Index, vol. 107, 1987, Formula C24H47NO6.

GLUCOSAMINE DERIVATIVE AND LIPOSOME CONTAINING THE SAME AS MEMBRANE CONSTITUENT

This application is a continuation of application Ser. No. 07/720,479 filed on Jul. 9, 1991, now abandoned.

TECHNICAL FIELD

The present invention relates to a novel glucosamine derivative useful as a membrane constituent of a cationic liposome, a cationic surfactant, and an antibody producing adjuvant.

The present invention also relates to a liposome containing the above novel glucosamine derivative as a membrane constituent.

BACKGROUND ART

A liposome is a hollow closed vesicle consisting of a lipid bilayer formed by suspending a thin membrane of polar lipid such as a phospholipid or the like in an aqueous solution. The liposome has basically the same lipid bilayer structure as that of a biomembrane and therefore is excellent in affinity to a living body. On the basis of this characteristic, studies on an application of the liposome as a drug delivery system have become a big concern. In this application, the liposome is used as a microcapsule having an affinity to a living body. That is, various types of drugs, enzymes or the like are administered to a living body as liposome preparations in which the drugs or the like is encapsulated.

A wide variety of drugs can be encapsulated in liposomes in accordance with the administration purpose of a liposome preparation, and an example is a superoxidedismutase (superoxide disproportionation enzyme; SOD) which inactivates a superoxide anion ($O_2^-$). The superoxide anion is produced by reduction of molecular oxygen in a living body in accordance with an external stimulus by which an antigen-antibody complex is formed. Since the superoxide anion has a function of oxidatively destroying a foreign matter phagocytosized by a phagocyte, it is effective in sterilization and detoxification. If, however, active oxygen such as the superoxide anion is produced in an excessive amount, it serves as a strong factor which causes tissue lesion or inflammation, resulting in rheumatism, an inflammatory disease such as Bechet syndrome or Crohn disease, diabetes mellitus, or a cancer disease (Drug Delivery System, 2(1), 1987). Therefore, administration of the SOD which inactivates the superoxide anion is effective in the therapy of these diseases.

The SOD, however, has low stability in a living body and has only a short half-life period in blood of about six minutes. In order to eliminate these drawbacks of the SOD, various attempts have been made to encapsulate the SOD in liposomes, thereby stabilizing the SOD and allowing to slowly deliver the encapsulated SOD. For example, Published Unexamined Japanese Patent Application No. 1-175944 teaches that the SOD is held by an electrically neutral or negative film of liposome, so as to stabilize the SOD. Also Published Unexamined Japanese Patent Application No. 63-211222 teaches that a liposome film component material containing phospholipid and chloesterol is hydrated at a temperature higher than the phase transition temperature, so as to take into the inner phase the physiologically active substance which tends to be denatured or deactivated by an enzyme drug such as the SOD. Further, each of Published Unexamined Japanese Patent Application Nos. 1-238537 and 1-246225 teaches that a polypeptide having the SOD activitates is prepared so as to facilitate intake of the polypeptide into a liposome and, thus, to prepare drugs for curing liver disorders and pancreatitis.

As a membrane constituent of the liposome, a lipid, especially a phospholipid such as lecithin is used. The phospholipid generally has a hydrophilic portion consisting of a phosphate ester residue and a hydrophobic portion consisting of a higher fatty acid residue. A phospholipid having eight or less, particularly, four or less carbon atoms in this fatty acid residue portion no longer forms any molecular aggregations. Therefore, no liposome can be formed from such a phospholipid. In order to form morphologically clear liposomes from a phospholipid, therefore, the number of carbon atoms of the fatty acid residue of the phospholipid must be ten or more, and preferably, 12 to 24. Note that, in general, a lipid other than a phospholipid, for example, triglyceride, cholesterol, cholesterolester, or $\alpha$-tocopherol is often added as an auxiliary for liposome formation.

For liposomes to be applied to a drug delivery system, there has been proposed a method of adding a small amount of a charged substance such as stearylamine as an assistant to a liposome so as to apply a positive electric charge to the membrane surface of the liposome. The purposes of the method are to improve a drug encapsulation ratio into the liposome and to improve the adhesion characteristics of the liposome with respect to cells. In addition, it is suggested that these cationic liposomes have better residence time in blood than those of neutral or anionic liposomes (Eur. J. Biochem., 47, 179-185 (1974)). The following two literatures can be exemplified as prior arts of this cationic liposome.

The first on is Published Unexamined Japanese Patent Application No. 63-77824 which discloses a cationic liposome medicinal preparation (L-SOD) encapsulating the SOD. In this L-SOD, stearylamine is used as a membrane constituent of the liposome in addition to dipalmitoylphosphatidylcholine and cholesterol.

The second one is "Drug Delivery System" (2(1), 41-52 (1987)) which discloses a cationic liposome medicinal preparation (L-SOD) also added with stearylamine.

Since, however, the above cationic L-SOD added with stearylamine has a serious problem of high toxicity, it causes a side effect of, e.g., convulsion when it is applied to a living body (J. Neurol. Sci., 31, 173-179 (1977)). For this reason, this cationic L-SOD has not been able to be put into practical use as a liposome medicinal preparation.

DISCLOSURE OF INVENTION

It is the first object of the present invention to provide a nontoxic novel glucosamine derivative usable as a membrane constituent of a liposome and serving as an agent for applying a positive charge to a liposome.

It is the second object of the present invention to provide a liposome comprising the above novel glucosamine derivative as a membrane constituent.

It is the third object of the present invention to provide a cationic liposome which can prolong a halftime period of a drug in blood by excellent residence properties and has a low toxicity.

The above first object of the present invention is achieved by a glucosamine derivative represented by the following formula [I] or a pharmacologically acceptable salt thereof:

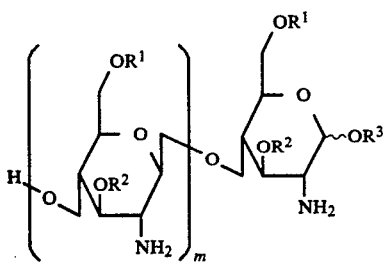

wherein $R^1$, $R^2$, $R^3$, and m represent the following
$R^1$ and $R^2$;
  a hydrogen atom or a $-CO(CH_2)_nCH_3$ group, n representing an integer from 10 to 22 and $R^1$ and $R^2$ being not simultaneoulsy hydrogen atoms
$R^3$;
  a hydrogen atom or a lower alkyl group, and
m;
  an integer from 0 to 3.

The second object of the present invention is achieved by a liposome containing, as one of membrane constituents, a glucosamine derivative represented by the above formula [I] or a pharmacologically acceptable salt thereof.

The third object of the present invention is achieved by a liposome comprising a liposome containing, as one of membrane constituents, a glucosamine derivative represented by the above formula [I] or a pharmacologically acceptable salt thereof, and a pharmacologically or physiologically active substance contained in a vesicle of the liposome.

The present invention will be described in detail below.

The present inventors have found that a glucosamine derivative represented by the above formula [I] and its pharmacologically allowable salt are useful as additives, especially, positive charge applying agents for a liposome membrane. The present inventors have also found that a cationic liposome prepared by using this glucosamine derivative or its pharmacologically acceptable salt can prolong a half-time period of a drug in blood because it is excellent in residence time in blood and that the liposome has a low toxicity. The present invention has been completed on the basis of these findings.

Note that it is assumed that a glucosamine derivative represented by formula [I] and a pharmacologically acceptable salt thereof are useful as not only positive charge applying agents for a liposome but also adjuvants for use in antibody production or as cationic surfactants.

The lower alkyl group represented by $R^3$ in formula [I] means a methyl group, an ethyl group, a propyl group, an isopropyl group, a butyl group, or an alkyl group having one to four carbon atoms, and most preferably, a methyl group.

A compound represented by formula [I] can produce a pharmacologically acceptable salt between an inorganic acid such as hydrochloric acid, sulfuric acid, or phosphoric acid, or an organic acid such as tartaric acid, maleic acid, fumaric acid, or succinic acid.

A compound represented by formula [I] is basically constituted by a hydrophobic portion ($R^1$ and $R^2$) consisting of a higher fatty acid residue and a hydrophilic portion consisting of a glucosamine residue. That is, since the higher fatty acid residues $R^1$ and $R^2$ in the 3-and 6-positions are groups for imparting hydrophobic characteristics to molecules, they need only be carbon chains enough to impart the hydrophobic properties. For example, similar to a phospholipid which constitutes a large proportion of a liposome, each of $R^1$ and $R^2$ is preferably a higher fatty acid residue having ten or more carbon atoms, and preferably, 12 to 24 carbon atoms (n=10 to 22). Since the glucosamine residue portion is a portion for imparting hydrophilic characteristics to molecules, this portion may have any number of glucosamine units as long as it does not interfere with the formation of liposomes. The portion is, however, preferably a monomer (m=0), a dimer (m=1), a trimer (m=2), or a tetramer (m=3), and most preferably, a monomer or a dimer. Note that the $-OR^3$ group on the 1-position does not directly contribute to the formation of liposomes or a positive charge of the liposomes. Therefore, $R^3$ may be either a hydrogen atom or a lower alkyl group.

Typical examples of a compound represented by formula [I] will be presented below, but the compound is not limited to these examples.

6-O-lauroyl-D-glucosamine methylglycoside
6-O-myristoyl-D-glucosamine methylglycoside
6-O-palmitoyl-D-glucosamine methylglycoside
6-O-stearoyl-D-glucosamine methylglycoside
3,6-di-O-lauroyl-D-glucosamine methylglycoside
3,6-di-O-myristoyl-D-glucosamine methylglycoside
3,6-di-O-palmitoyl-D-glucosamine methylglycoside
3,6-di-O-stearoyl-D-glucosamine methylglycoside
6,6'-di-O-palmitoyl-D-glucosamino-(1→4)-β-D-glucosamine methylglycoside
3-O-palmitoyl-D-glucosamine methylglycoside
6-O-palmitoyl-D-glucosamine Glucosamine derivative [I] according to the present invention has a high affinity to a phospholipid such as lecithin. In addition, since glucosamine derivative [I] has an amino group in the 2-position, when it is added to a phospholipid such as lecithin so as to be used as a membrane constituent, a positive charge can be applied to a formed liposome. Therefore, glucosamine [I] is very useful as an auxiliary, especially, a positive charge applying agent for liposome formation. Furthermore, since glucosamine derivative [I] is comprises a hydrophobic portion consisting of a higher fatty acid residue and a hydrophilic portion consisting of a glucosamine residue, its usefulness as a cationic surfactant or an antibody producing adjuvant is also expected.

A method of preparing glucosamine derivative [I] of the present invention will be described below. Although this preparing method is not particularly limited, an example of the method is as follows. Note that in the following synthesis flow, $R^1$, m and n have the same meanings as described above and Z represents a benzyloxycarbonyl group used as a protective group of an amino group.

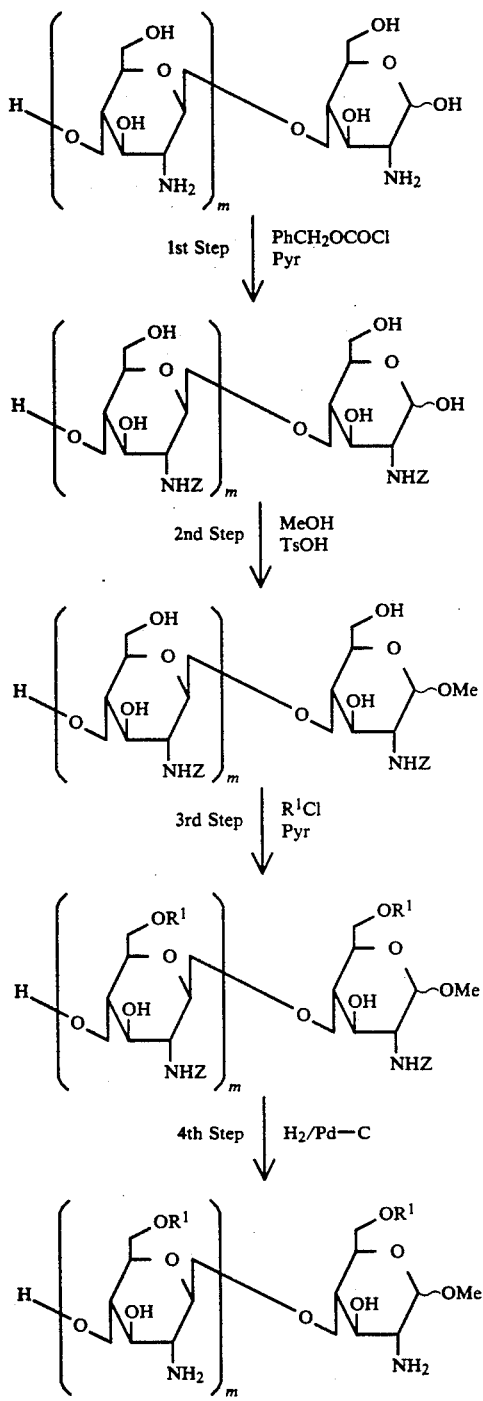

The above synthesis flow exemplifies a method of preparing glucosamine derivative [I] having the following $R^1$ and $R^2$.

$R^1$: —CO(CH$_2$)$_n$CH$_3$ $R^2$: hydrogen atom

In order to prepare glucosamine derivative [I] in which both $R^1$ and $R^2$ are —CO(CH$_2$)$_n$CH$_3$ groups, two or more mols of ClCO(CH$_2$)$_n$CH$_3$ are used per N-benzyloxycarbonylglucosamine residue in compound [IV] in the third step. In order to prepare glucosamine derivative [I] in which $R^1$ and $R^2$ are different acyl groups, after the reaction shown in the third step, another $R^2$Cl is reacted with the reaction product. In order to prepare glucosamine derivative [I] in which $R^1$ is a hydrogen atom and $R^2$ is a —CO(CH$_2$)$_n$CH$_3$ group in contrast to the above flow, after the hydroxyl group at the 6-position of compound [IV] in the third step, $R^2$Cl is reacted with the reaction product.

Each step of the synthesis shown in the above flow will be described in detail below.

1st Step

A known amino sugar represented by formula [II] or its hydrochloride is reacted with benzyloxycarbonylchloride (PhCH$_2$OCOCl) in a solvent such as pyridine. As a result, the amino group at the 2-position of amino sugar [II] is protected by a benzyloxycarbonyl group (Z) to obtain compound [III].

2nd Step

Compound [III] obtained in the first step is reacted with methanol using p-toluenesulfonic acid or the like as a catalyst. As a result, the 1-position of compound [III] is methoxylated to obtain compound [IV].

Note that monomeric compound [IV] of m=0 is a known compound or a compound which can be derived very easily from the known compound by those skilled in the art in accordance with conventional methods.

When compound [III] is an oligomer of m=1 to 3, a glycoside bond between glucosamine monomers is susceptible to be broken if the compound is directly methoxylated. Therefore, the following method is preferably used to prevent the breaking of this glycoside bond. First, compound [III] and acetic anhydride are reacted in a solvent such as pyridine to protect all hydroxyl groups of compound [III] with acetyl groups. Subsequently, a small amount of a hydrobromic acid/acetic acid solution is added, and the resultant solution is further reacted in a methanol solvent under the presence of silver carbonate, thereby selectively substituting the acetoxyl group at the 1-position with a methoxy group. Thereafter, this compound in which the 1-position is methoxylated is reacted in a methanol solvent in the presence of sodium carbonate. With this reaction, the residual acetyl group is eliminated and converted into a hydroxyl group to obtain compound [IV]. A series of these manipulations are represented by the following formulas.

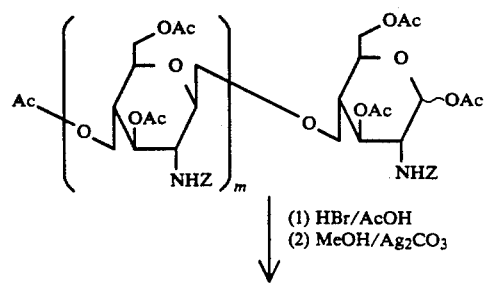

-continued

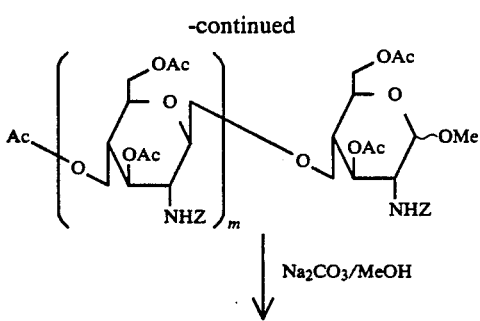

Compound [IV]

3rd Step

Compound [IV] obtained in the second step and higher fatty acid chloride $(CH_3(CH_2)_nCOCl)$ are reacted in a solvent such as pyridine to esterify the hydroxyl group at the 6-position of compound [IV] to obtain compound [V]. The amount of the higher fatty acid is one mol per N-benzyloxycarbonylglucosamine residue of compound [IV]. Note that in order to simultaneously esterify the hydroxyl group at the 3-position, two or more mols of higher fatty acid chloride are used per N-benzyloxycarbonylglucosamine residue, as described above.

4th Step

Hydrogenation of compound [V] obtained in the third step is performed in the presence of a catalyst such as Pd-C, thereby dissociating the Z group. As a result, final target compound [I'] is obtained.

Note that the preparing method exemplified above relates to compound [I] having a lower alkoxy group at the 1-position (i.e., $R^3$ is a lower alkyl group). However, when compound [I] having the lower alkoxy group at the 1-position prepared as described above is hydrolyzed using a known suitable means such as a hydrolytic enzyme, compound [I] having a hydroxyl group at the 1-position (i.e., $R^3$ is a hydrogen atom) can be easily prepared. In addition, the preparing method may be performed such that a synthesis reaction similar to that described above is performed while the hydroxyl group at the 1-position is protected by a suitable protective group and the protective group is eliminated in the final stage.

A liposome according to the present invention will be described below.

In general, a liposome consisting of a lipid bilayer is classified into the following three types on the basis of its structure. However, the liposome of the present invention may take any of these structures.

① A liposome having a multiconcentric lamellar structure (a multilamellar vesicle; MLV)
② A liposome having a small unilamellar structure (a small unilamellar vesicle; SUV)
③ A liposome having a large unilamellar structure (a large unilamellar vesicle; LUV)

As has been described above, the liposome according to the present invention is characterized by containing novel glucosamine derivative [I] as a membrane constituent. However, any lipid normally used in the formation of liposomes can be additionally used as the membrane constituent. Examples of the lipid are natural and synthetic phospholipids such as phosphatidylglycerol, phosphatidynic acid, phosphatidylcholine, phosphatidylethanolamine, phosphatidylserine, phosphatidylinositol, sphingomyelin, yolk lecithin, and soybean lecithin, a hydrogenated phospholipid, and a glycero sugar lipid. These lipids may be used singly or in a combination of two or more types thereof.

In addition, a sterol-based stabilizer such as cholesterol may be mixed in order to stabilize the membrane structure. Furthermore, an antioxidant such as tocopherol or $\beta$-carotin and other additives can be arbitrarily mixed.

In the liposome of the present invention, a ratio between the membrane constituent is not particularly limited. In general, a use amount of glucosamine derivative [I] with respect to 100 parts by weight of a phospholipid is 0.5 to 30, and preferably, 1 to 25 parts by weight. If the amount of the glucosamine derivative is less than 0.5 parts by weight, no satisfactory effect as a cationic liposome can be obtained. If the mixing amount of glucosamine derivative [I] exceeds 30 parts by weight, the liposome forming capability may be decreased. Since the effect as a cationic liposome is not much enhanced even if glucosamine derivative [I] is used in an amount of more than 30 parts by weight, the use of a large amount of the glucosamine derivative is meaningless in terms of cost. The mixing amount of a stabilizer such as cholesterol is generally 30 parts by weight or less with respect to 100 parts by weight of a phospholipid. The use amount of other additives such as an antioxidant is generally five parts by weight or less.

The particle size of the liposomes of the present invention is not particularly limited but may be arbitrarily selected in accordance with the individual applications. However, the particle size is preferably 0.3 $\mu$m or less, and more preferably, 0.2 $\mu$m or less.

According to the liposome of the present invention, various types of useful pharmacologically or physiologically active substances are contained in the lamellar structure of the liposome described above. Although the SOD has been exemplified as a drug to be contained in the liposome of the present invention, the drug is not limited to the SOD but various types of water- or lipid-soluble drugs can be used. Note that since the liposome itself has a positive charge, a drug which is electrically neutral or anionic is preferable. Preferable examples of such a drug are, in addition to the SOD, an anti-inflammatory drug such as indomethacin, an oxygen carrier drug such as hemoglobin, an enzyme drug such as Urokinase, an antibiotic substance such as doxycycline hydrochloride or gentamicin sulfate, and hormone drugs such as insulin, ACTH (adrenocorticotropic hormone), or calcitonin. In addition, an anticancer drug can be exemplified as a drug which effectively utilizes a long residence time in blood as the merit of the liposome of the present invention.

The liposomes of the present invention can be prepared by conventional methods normally used in this field of art. An example of the methods will be described below.

First, a phospholipid, a glucosamine derivative, and other membrane constituent such as a membrane stabilizer, a charged substance, and an antioxidant, if necessary, are dissolved in an organic solvent, and the resultant solution is poured in a flask. Subsequently, the solvent is distilled off at a reduced pressure to form a lipid thin membrane on the inner surface of the flask, and vacuum drying is then performed. A drug solution prepared by adding a desired drug to a suitable buffer solution such as tris-hydrochloric acid is poured in the flask so that the lipid thin membrane formed on the inner surface of the flask swells. At the same time, shaking (preferably an ultrasonic treatment) is performed to form a dispersion. In this dispersion, the lipid thin membrane forms liposomes encapsulating the drug solution. Thereafter, centrifugal separation, gel filtration, or ultrafiltration is performed to remove the residual drug solution not encapsulated in the liposomes. The drug-encapsulating liposomes thus obtained are redispersed in an isotonic buffer solution. This drug-encapsulating liposome dispersion can be directly used as an injection drug. However, the dispersion may be lyophilized as needed so that it can be dispersed in a medium and prepared into an injectable solution upon usage. In addition, if particle size control of the liposomes is required, it can be performed by arbitrarily using conventional methods such as a pressure filtration method (extruder method), gel filtration, and centrifugal separation.

BEST MODE OF CARRYING OUT THE INVENTION

The present invention will be described in more detail below by way of its examples.

Example 1 (Preparation of 6-O-palmitoyl-D-glucosamine methylglycoside)

(1) Preparation of N-benzyloxycarbonyl-6-O-palmitoyl-D-glucosamine methylglycoside

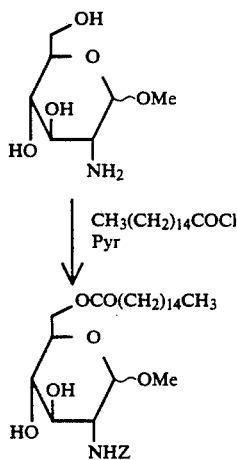

N-benzyloxycarbonyl-D-glucosamine methylglycoside 1 was obtained from D-glucosamine in accordance with a conventional method. This N-benzyloxycarbonyl-D-glucosamine methylglycoside 1 (9.3 g) and palmitoylchloride 2 (8 ml) were added to pyridine (50 ml), and reacted under stirring in a nitrogen gas atmosphere at room temperature for 24 hours. The reaction mixture was poured into 10% hydrochloric acid with ice-cooling and extracted by ethyl acetate. Thereafter, the extract was washed successively with saturated sodium bicarbonate ($NaHCO_3$) and a brine (sodium chloride solution), and dried with anhydrous sodium sulfate ($Na_2SO_4$). The solvent was removed from the dried solution to obtain a crude product. The obtained crude product was recrystallized from an ethyl acetate solution to obtain N-benzyloxycarbonyl-6-O-palmitoyl-D-glucosamine methylglycoside 3 (7.65 g). The yield was 52%. Physical data of the product are as follows.

m.p.: 96° C. to 97° C.

IR (KBr): 3,330 $cm^{-1}$, 3,030 $cm^{-1}$, 2,920 $cm^{-1}$; 2,850 $cm^{-1}$, 1,735 $cm^{-1}$, 1,690 $cm^{-1}$; 1,540 $cm^{-1}$, 1,460 $cm^{-1}$, 1,260 $cm^{-1}$.

MS (FAB): 566 $(M+1)^+$.

1H-NMR (DMSO-$d_6$); δ (ppm): 7.36 (s,5H); 7.12 (d,J=8Hz,1H); 5.25 (d,J=7.4Hz,1H); 5.03 (s,2H); 4.90 (d,J=4Hz,1H); 4.58 (d,J=2.4Hz,1H); 4.32 (d,J=12.4Hz,1H); 4.07 (dd,J=6.2Hz,J=6.6Hz,1H); 3.40-3.6 (m,2H); 3.24 (s,3H); 3.15 (m,1H); 2.31 (t,J=7Hz,2H); 1.51 (m,2H); 1.24 (b,24H); 0 86 (t,J=6.2Hz,3H).

$^1$H-NMR (CDCl$_3$): δ (ppm): 7.36 (s, 5H); 5.18 (d,J=8.8Hz,1H); 4.71 (d,J=3.6 Hz,1H); 4.50 (dd,J=4 Hz,1H); 4.25 (d,J=12.4 Hz,1H); 3.6-3.9 (m,2H); 3.35 (s,3H); 2.37 (t,J=7.4 Hz,2H); 1.63 (m,2H); 1.25 (b,24H); 0.88 (t,J=6Hz,3H)

(2) Preparation of 6-O-palmitoyl-D-glucosamine methylglycoside

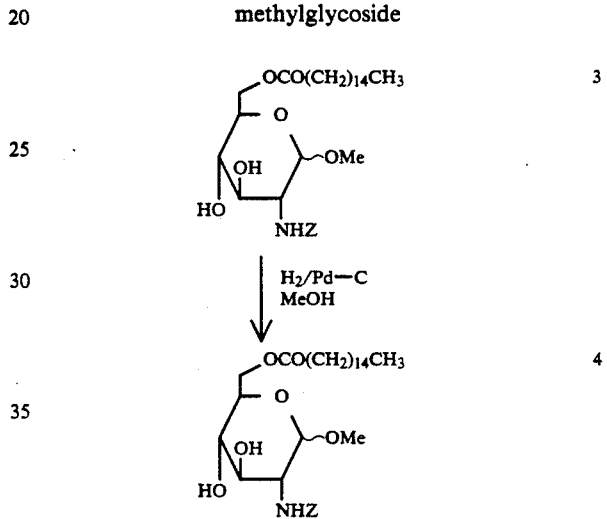

N-benzyloxycarbonyl-6-O-palmitoyl-D-glucosamine methylglycoside 3 (1.35 g) obtained as described above was dissolved in methanol (50 ml), and a catalytic amount of 5% Pd-C was added to perform contact reduction at room temperature under atmospheric pressure for 24 hours. After completion of the reaction, the resultant material was filtered to remove the solvent. Subsequently, the residue was purified by a column chromatography to obtain 6-O-palmitoyl-D-glucosamine methylglycoside 4 (874 mg) as a target compound. The yield was 85%.

m.p.: 70.5° C. to 71.5° C.

| Elemental analysis: | C | H | N |
|---|---|---|---|
| Measured value | 64.24% | 10.84% | 3.04% |
| Calculated value* | 64.00% | 10.51% | 3.25% |

(*A calculated value for $C_{23}H_{43}O_6N$)

IR (KBr): 3,350 $cm^{-1}$, 2,920 $cm^{-1}$, 2,850 $cm^{-1}$, 1,730 $cm^{-1}$, 1,460 $cm^{-1}$.

MS (FAB): 432 $(M+1)^+$.

$^1$H-NMR (DMSO-$d_6$): δ (ppm): 5.15 (m,1H); 5.00 (m,1H); 4.51 (d,J=3.4Hz,1H); 4.30 (d,J=10.6Hz,1H); 4.04 (dd,J=6.6Hz,J=6.8Hz,1H); 3.53 (m,1H); 3.26 (s,3H); 3.10 (m,2H); 2.40 (m,1H); 2.29 (t,J=7.2Hz,2H); 1.51 (m,2H); 1.24 (b,24H); 0.86 (t,J=6.0Hz,3H).

EXAMPLE 2 (PREPARATION OF 6-O-LAUROYL-D-GLUCOSAMINE METHYLGLYCOSIDE)

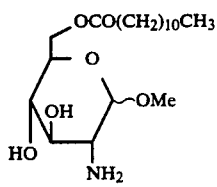

The above compound was prepared as an oily substance, following the same procedures as in Example 1 except that lauroylchloride was used in place of palmitoylchloride. Elemental analysis values of the product were as follows.

| Elemental analysis: | C | H | N |
|---|---|---|---|
| Measured value* | 60.34% | 9.95% | 3.63% |
| Calculated value* | 60.80% | 9.87% | 3.73% |

(*A calculated value for $C_{19}H_{37}O_6N$)

EXAMPLE 3 (PREPARATION OF 6-O-MYRISTOYL-D-GLUCOSAMINE METHYLGLYCOSIDE)

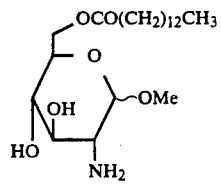

The above compound was prepared following the same procedures as in Example 1 except that myristoylchloride was used in place of palmitoylchloride. The melting point and elemental analysis values of the product were as follows.

m.p.: 65° C. to 70° C.

| Elemental analysis: | C | H | N |
|---|---|---|---|
| Measured value: | 62.18% | 10.27% | 3.33% |
| Calculated value:* | 62.53% | 10.17% | 3.47% |

(*A calculated value for $C_{21}H_{41}O_6N$)

EXAMPLE 4 (PREPARATION OF 6-O-STEAROYL-D-GLUCOSAMINE METHYLGLYCOSIDE)

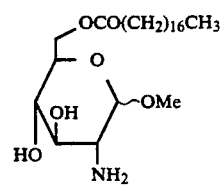

The above compound was prepared following the same procedures as in Example 1 except that stearoylchloride was used in place of palmitoylchloride. The mass spectrum analysis value of the product was as follows.

MS: 459.3542 (M+).
(A Calculated value for $C_{25}H_{49}O_6N$; 459.3559).

EXAMPLE 5 (PREPARATION OF 6,6'-DI-O-PALMITOYL-D-GLUCOSAMINO-(1→4)-β-D-GLUCOSAMINE METHYLGLYCOSIDE)

(1) Preparation of N,N'-dibenzyloxycarbonyl-D-glucosamino-(1→4)-β-D-glucosamine

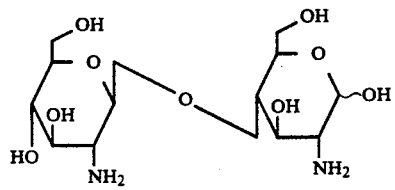

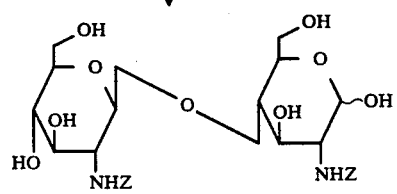

D-glucosamino-(1→4)-β-D-glucosamine hydrochloride 1 (2.5 g) and sodium bicarbonate (2.1 g) were dissolved in a solvent mixture (water : methanol = 3:4 v/v, 70 ml). Benzyloxycarbonylchloride (PhCH$_2$OCOCl) (2.4 g; 2 ml) was added to the resultant solution, and the solution was stirred at room temperature for two hours. The product was filtered off, washed with purified water and dichloromethane twice each, and dried in a vacuum. The resultant product was recrystallized from methanol to obtain N,N'-dibenzyloxycarbonyl-D-glucosamino-(1→4)-β-D-glucosamine 2 (62 mg). The yield was 72.6%. Physical data of the product was as follows. $^1$H-NMR (DMSO-d$_6$): δ (ppm): 3.11–3.72 (m,10H); 4.5 (tetra,J=5.34 Hz,1H); 4 32 (d,J=7.04Hz,1H); 4.45 (s,1H); 4.55 (s,1H); 4.71 (s,1H); 4.94–5.13 (m,8H); 6.56 (d,J=4.3Hz,1H); 7.20 (d,J=8.36Hz,2H); 7.36 (s,10H).

IR (KBr): 3,325 cm$^{-1}$, 2,940 cm$^{-1}$, 1,680 cm$^{-1}$, 1,540 cm$^{-1}$, 1,280 cm$^{-1}$, 1,245 cm$^{-1}$, 1,030 cm$^{-1}$.

MS (FAB): 609 (M+1)+.

(2) Preparation of N,N'-dibenzyloxycarbonyl-3,4,6,1',3',6',-hexa-O-acetyl-D-glucosamino-(1→4)-β-D-glucosamine

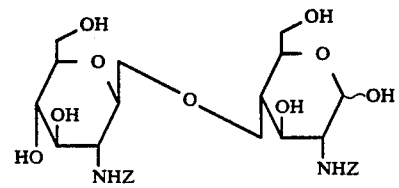

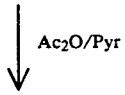

-continued

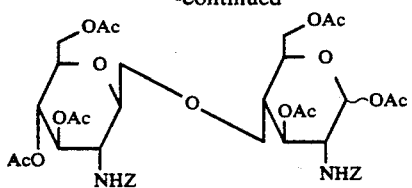

The compound 2 (1.5 g) obtained in item (1) above was dissolved in pyridine (15 ml). Acetic anhydride (10 ml; about 0.11 mol) was added to the resultant solution, and the solution was stirred at room temperature for 12 hours to cause a reaction. After the reaction, 10% hydrochloric acid was added, and extracted with ethyl acetate. The extract was washed with saturated sodium chloride solution and dried with anhydrous sodium sulfate. Subsequently, the solvent was removed to obtain N,N'-dibenzyloxycarbonyl-3,4,6,1',3',6'-hexa -O-acetyl-D-glucosamino-(1→4)-β-D-glucosamine 3 (1.88 g). The yield was 87.04%. $^1$H-NMR of the product was as follows.

$^1$H-NMR (CDCl$_3$); δ (ppm): 1.89 (s,3H); 1.92 (s,3H); 1.95 (s,3H); 1.99 (s,3H); 2.07 (s,3H); 2.08 (s,3H); 3.61–4.40 (m,9H); 4.97–5.34 (m,10H); 6.13 (d,J=3.66Hz,1H); 7.33 (s,10H).

(3) N,N'-dibenzyloxycarbonyl-3,4,6,3',6'-penta -O-acetyl-D-glucosamino-(1→4)-β-D-glucosamine methylglycoside

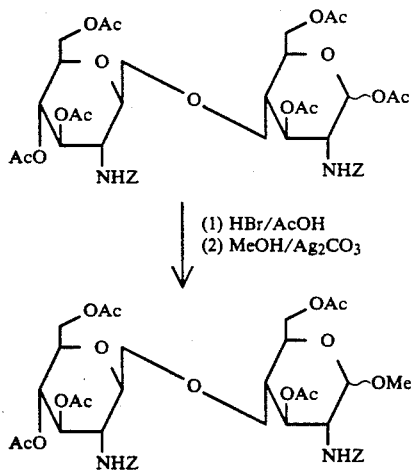

The compound 3 (1.5 g) obtained in item (2) described above was dissolved in dried dimethylchloride (30 ml). A 25% hydrobromic acid/acetic acid solution (1.5 ml) was added at 0° C., and the resultant solution was stirred in a nitrogen gas atmosphere for four hours. After completion of the reaction, the reaction mixture was put into ice water to remove the hydrobromic acid, and extracted with dichloromethane. Subsequently, the extract was dried with anhydrous sodium sulfate, and dichloromethane was distilled off to obtain a crude product. The obtained crude product was immediately dissolved in dried methanol. Silver carbonate was added to the resultant solution, and the solution was stirred at room temperature for 24 hours. After silver carbonate was removed by filtration, methanol was distilled off. The obtained crude product (1.22 g) was purified by using a column chromatography to obtain N,N'-dibenzyloxycarbonyl-3,4,6,3',6'-penta -O-acetyl-D-glucosamino-(1→4)-β-D-glucosamine methylglycoside 4 (0.52 g). The yield was 35.8%. $^1$H-NMR of the product was as follows.

$^1$H-NMR (CDCl$_3$): δ (ppm): 1.91 (s,3H); 1.92 (s,3H); 1.99 (s,3H); 2.06 (s,3H); 2.08 (s,3H); 3.47 (s,3H); 3.52–3.74 (m,4H); 3.98-4.37 (m,6H); 4.96–5.28 (m,10H); 7.32 (s,10H).

(4) Preparation of N,N'-dibenzyloxycarbonyl -D-glucosamino-(1→4)-β-D-glucosamine methylglycoside

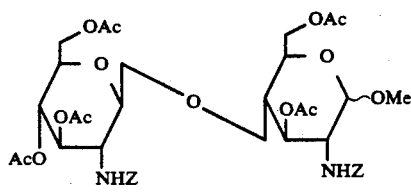

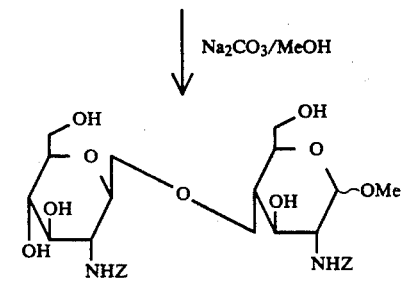

Methanol (30 ml) was added to the compound 4 (1.0 g) obtained in item (3) described above, and the resultant solution was stirred to prepare a suspension. Saturated sodium carbonate (3 ml) was added to the suspension to cause a reaction for 24 hours, and the suspension was extracted by ethyl acetate to obtain N,N'-dibenzyloxycarbonyl-D-glucosamino-(1→4)-β-D-glucosamine methylglycoside 5 (0.45 g). The yield was 60%. $^1$H-NMR of the product was as follows.

$^1$H-NMR (DMSO-d6): δ (ppm): 3.06–3.70 (m,7H); 4.12-4.16 (m,2H); 4.99–5.28 (m,6H); 4.52–4.68 (m,1H); 5.26–5.28 (m,2H); 7.36 (s,10H).

(5) Preparation of N,N'-dibenzyloxycarbonyl-6,6'-di -O-palmitoyl-D-glucosamino-(1→4)-β-D-glucosamine methylglycoside

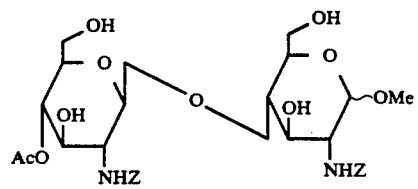

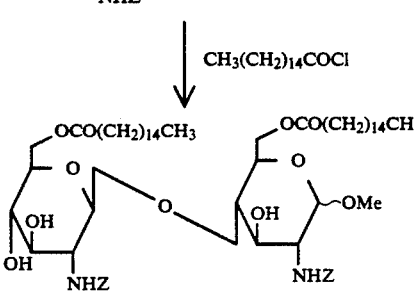

The compound 5 (0.3 g) obtained in item (4) described above was dissolved in pyridine (5 ml). While the resultant solution was stirred in a nitrogen gas atmosphere, palmitoylchloride (0.29 g; 0.3 ml) was added to cause a reaction at from 0° C. to room temperature for 12 hours. After completion of the reaction, a 10% aqueous hydrochloric acid was added, and the resultant solution was extracted with ethyl acetate. The extract was washed with saturated sodium chloride solution, and the solvent was distilled off to obtain a crude product (0.58 g). The obtained crude product was purified by using a column chromatography to obtain N,N'-dibenzyloxycarbonyl-6,6'-di-O-palmitoyl -D- glucosamino-(1→4)-β-D-glucosaminemethylglycoside 6 (0.1 g). The yield was 19.17%. $^1$H-NMR of the product was as follows.

$^1$H-NMR (DMSO-d$_6$): δ (ppm): 0.83–0.88 (m,6H); 1.23 (s,54H); 1.51 (m,4H); 2.27 (m,5H); 3.35–3.48 (m,11H); 3.97–4.61 (m,6H); 4.90–5.05 (m,4H); 7.33 (s,10H).

(6) Preparation of 6,6'-di-O-palmitoyl-D-glucosamino-(1→4)-β-D-glucosamine methylglycoside

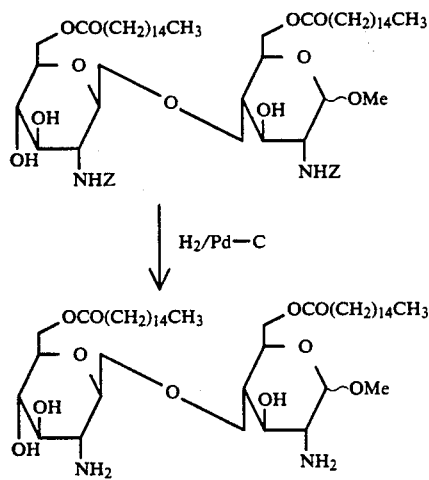

The compound 6 (0.16 g) obtained in item (5) described above was added to a solvent mixture (tetrahydrofuran : methanol=1 : 1 v/v, 10 ml) and dissolved therein by stirring. Pd-C was added to the resultant solution, and the solution was reacted with hydrogen gas at room temperature for 12 hours. After completion of the reaction, the reaction mixture was filtered to remove Pd-C, and the solvent was distilled off to obtain a crude product (0.11 g). The obtained curde product was purified by using pre-TLC to obtain a final product 6,6'-di-O-palmitoyl-D-glucosamino-(1→4)-β-D-glucosamine methylglycoside 7 (0.02 g). The yield was 16.7%. The mass spectrum analysis and the IR of the product were as follows.

MS (FAB): 831 (M+1)$^+$,

IR (KBr): 3,420 cm$^{-1}$, 2,920 cm$^{-1}$, 2,850 cm$^{-1}$, 1,740 cm$^{-1}$, 1,470 cm$^{-1}$,

EXAMPLE 6 (PREPARATION OF 3,6-DI-O-LAUROYL-D-GLUCOSAMINE METHYLGLYCOSIDE)

(1) Preparation of N-benzyloxycarbonyl-3,6-di-O-lauroyl-D-glucosamine methylglycoside

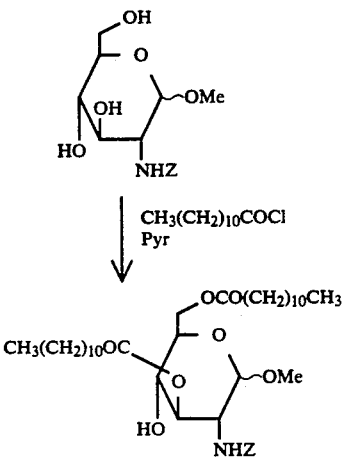

N-benzyloxycarbonyl-D-glucosamine methylglycoside 1 (10 g; 30.58 mmol) obtained from D-glucosamine hydrochloride in accordance with a conventional method was dissolved in pyridine (60 ml). Lauroylchloride (14.71 g; 67.3 mmol) was added to the resultant solution at room temperature, and the solution was stirred for hours. 10% aqueous hydrochloric acid was added, and the resultant solution was extracted with ethyl acetate. The ethyl acetate layer was washed with saturated sodium chloride solution. Ethyl acetate was distilled off from this extract to obtain a crude product (19.3 g). This crude product was purified by using a column chromatography to obtain N-benzyloxycarbonyl-3,6-di-O-lauroyl-D-glucosamine methylglycoside 2 (2.7 g). The yield was 15.06%.

(2) Preparation of 3,6-di-O-lauroyl-D-glucosamine methylglycoside

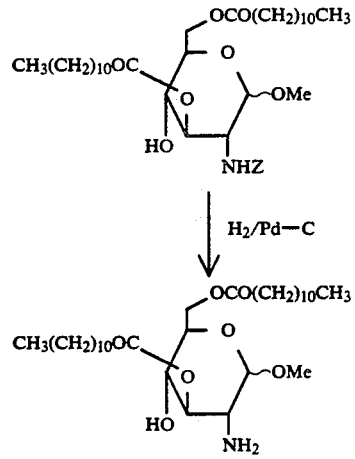

The compound 2 (2.7 g; 3.14 mmol) obtained in item (1) described above was dissolved in a solvent mixture (methanol : ethyl acetate=1 : 1 v/v). Pd-C as a catalyst was added to the resultant solution, and the solution was reacted with hydrogen gas for ten hours. After the reaction, the catalyst was removed by filtration to obtain a crude product (1.85 g). The crude product was purified by using a column chromatography to obtain 3,6-di-O-lauroyl-D-glucosamine methylglycoside 3 (0.5 g). The yield was 28.6%. Physical data of the product was as follows.

m.p.: 50° C. to 54° C.

IR (KBr): 3,380 cm$^{-1}$, 2,940 cm$^{-1}$, 2,860 cm$^{-1}$; 1,730 cm$^{-1}$, 1,580 cm$^{-1}$, 1,470 cm$^{-1}$; 1,190 cm$^{-1}$, 1,100 cm$^{-1}$, 1,060 cm$^{-1}$.

$^1$H-NMR (CDCl$_3$): δ (ppm): 0.88 (t,J=6.14Hz,6H); 1.26 (s,36H); 1.60–1.66 (m,4H); 2.09 (s,3H); 2.31–2.44 (m,2H); 2.83–2.90 (m,1H); 4.26–4.49 (m,1H); 4.74–4.99 (m,1H); 3.35–3.45 (m,4H); 3.77–3.79 (m,1H).

| Elemental analysis: | C | H | N |
| --- | --- | --- | --- |
| Measured value | 66.40% | 10.81% | 2.32% |
| Calculated value | 66.78% | 10.59% | 2.51% |

(A calculated value for C$_{31}$H$_{59}$O$_7$N)

EXAMPLE 7 (PREPARATION OF 3,6-DI-O-MYRISTOYL-D-GLUCOSAMINE METHYLGLYCOSIDE)

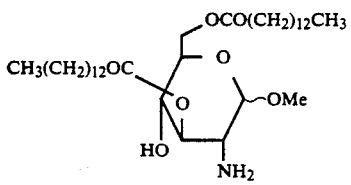

The above compound was prepared following the same procedures as in Example 6 except that myristoyl-chloride was used in place of lauroylchloride. The yield was 35.54%. Physical data of the product was as follows.

m.p.: 47° C. to 50° C.

IR (KBr): 3,380 cm$^{-1}$, 2,940 cm$^{-1}$, 2,860 cm$^{-1}$; 1,730 cm$^{-1}$, 1,580 cm$^{-1}$, 1,470 cm$^{-1}$; 1,190 cm$^{-1}$, 1,100 cm$^{-1}$, 1,060 cm$^{-1}$.

$^1$H-NMR (CDCl$_3$): δ (ppm): 0.88 (t,J=6.16Hz,6H); 1.26 (s,42H); 1.58–1.70 (m,4H); 1.87–1.93 (m,2H); 2.34–2.45 (m,4H); 2.83–2.90 (m,1H); 3.36–3.45 (m,4H); 3.77–3.84 (m,1H); 4.26–4.52 (m,1H); 4.75 (d,J=3.52Hz,1H); 4.94 (t,J=9.7Hz,1H).

| Elemental analysis: | C | H | N |
| --- | --- | --- | --- |
| Measured value | 68.43% | 11.14% | 2.02% |
| Calculated value* | 68.52% | 10.93% | 2.28% |

(*A calculated value for C$_{35}$H$_{67}$O$_7$N)

EXAMPLE 8 (PREPARATION OF 3,6-DI-O-STEAROYL-D-GLUCOSAMINE METHYLGLYCOSIDE)

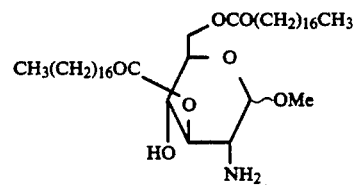

The above compound was prepared following the same procedures as in Example 6 except that stearoyl-chloride was used in place of lauroylchloride. The yield was 22.27%. Physical data of the product was as follows.

IR (KBr): 3,380 cm$^{-1}$, 2,940 cm$^{-1}$, 2,860 cm$^{-1}$; 1,730 cm$^{-1}$, 1,580 cm$^{-1}$, 1,470 cm$^{-1}$; 1,190 cm$^{-1}$, 1,100 cm$^{-1}$, 1,060 cm$^{-1}$.

$^1$H-NMR (CDCl$_3$): δ (ppm): 0.88 (t,J=6.21Hz,6H); 1.25 (s,58H); 1.52–1.65 (m,4H); 2.00–2.13 (m,2H); 2.33–2.45 (m,4H); 2.82–2.89 (m,1H); 3.35–3.55 (m,4H); 3.77–3.83 (m,1H); 4.27–4.50 (m,1H); 4.75 (d,J=3.28Hz,1H); 4.94 (t,J=9.52Hz,1H).

MS: 725.6155 (M+.)

(A calculated value for C$_{43}$H$_{83}$O$_7$N; 725.6167).

EXAMLE 9 (LIPOSOME CONTAINING 6-O-PALMITOYL-D-GLUCOSAMINE METHYLGLYCOSIDE AS A MEMBRANE CONSTITUENT)

The following three types of membrane constituents each of which was used as chloroform solution were poured and mixed in an eggplant type flask with a volume of 50 ml.

Phosphatidylcholine (concentration=100 mM); 840 μl

Cholesterol (concentration=100 mM); 240 μl

6-O-palmitoyl-D-glucosamine methylglycoside (concentration=10 mM); 1,200 μl The molar ratio between the above three components is 7 : 2 : 1. In addition, 10 ml of chloroform were added.

After chloroform was distilled off, the resultant material was dried in a vacuum over night to form a thin lipid membrane on the inner wall of the flask. Subsequently, 60 μl of a bovine erythrocyte-derived SOD dissolved in 3,940 μl of 300-mM sorbitol/10-mM trishydrochloric acid buffer solution (the content=30 μg/ml) were added into the flask, and the resultant solution was strongly shaken and stirred to prepare a liposome (MLV) dispersion. The prepared dispersion was left to stand at room temperature for two hours and was then left to stand at about 20° C. over night while the light was shielded. A 300-mM sorbitol/10-mM trishydrochloric acid buffer solution was used to make a total amount of 12 ml, and the resultant solution was subjected to centrifugal separation (about 120,000 g, 70 minutes). The supernatant liquid was decanted to remove a non-encapsulated SOD, thereby obtaining pellets of liposomes. The obtained pellets were dispersed in 100 ml of a 300-mM sorbitol/10-mM tris-hydrochloric acid buffer solution to prepare dispersion of the above liposome holding the SOD.

EXAMPLE 10 (LIPOSOME CONTAINING 6-O-LAUROYL-D-GLUCOSAMINE METHYLGLYCOSIDE)

The above liposome dispersion was prepared following the same procedures as in Example 9 except that 6-O-lauroyl-D-glucosamine methylglycoside was used in place of 6-O-palmitoyl-D-glucosamine methylglycoside.

EXAMPLE 11 (LIPOSOME CONTAINING 6-O-MYRISTOYL-D-GLUCOSAMINE METHYLGLYCOSIDE)

The above liposome dispersion was prepared following the same procedures as in Example 9 except that 6-O-myristoyl-D-glucosamine methylglycoside was used in place of 6-O-palmitoyl-D-glucosamine methylglycoside.

EXAMPLE 12 (LIPOSOME CONTAINING 6-O-STEAROYL-D-GLUCOSAMINE METHYLGLYCOSIDE)

The above liposome dispersion was prepared following the same procedures as in Example 9 except that 6-O-stearoyl-D-glucosamine methylglycoside was used in place of 6-O-palmitoyl-D-glucosamine methylglycoside.

EXAMPLE 13 (LIPOSOME CONTAINING 6,6'-DI-O-PALMITOYL-D-GLUCOSAMINO-(1→4)-β-D-GLUCOSAMINE METHYLGLYCOSIDE)

The above liposome dispersion was prepared following the same procedures as in Example 9 except that 6,6'-di-O-palmitoyl-D-glucosamino-(1→4)-β-D-glucosamine methylglycoside was used in place of 6-O-palmitoyl-D-glucosamine methylglycoside.

EXAMPLE 14 (LIPOSOME CONTAINING 3,6-DI-O-LAUROYL-D-GLUCOSAMINE METHYLGLYCOSIDE)

The above liposome dispersion wa prepared following the same procedures as in Example 9 except that 3,6-di-O-lauroyl-D-glucosamine methylglycoside was used in place of 6-O-palmitoyl-D-glucosamine methylglycoside.

EXAMPLE 15 (LIPOSOME CONTAINING 3,6-DI-O-MYRISTOYL-D-GLUCOSAMINE METHYLGLYCOSIDE)

The above liposome dispersion was prepared following the same procedures as in Example 9 except that 3,6-di-O-myristoyl-D-glucosamine methylglycoside was used in place of 6-O-palmitoyl-D-glucosamine methylglycoside.

EXAMPLE 16 (LIPOSOME CONTAINING 3,6-DI-O-PALMITOYL-D-GLUCOSAMINE METHYLGLYCOSIDE)

The above liposome dispersion was prepared following the same procedures as in Example 9 except that 3,6-di-O-palmitoyl-D-glucosamine methylglycoside was used in place of 6-O-palmitoyl-D-glucosamine methylglycoside.

EXAMPLE 17 (LIPOSOME CONTAINING 3,6-DI-O-STEAROYL-D-GLUCOSAMINE METHYLGLYCOSIDE)

The above liposome dispersion was prepared following the same procedures as in Example 9 except that 3,6-di-O-stearoyl-D-glucosamine methylglycoside was used in place of 6-O-palmitoyl-D-glucosamine methylglycoside.

EXAMPLE 18 (LIPOSOME CONTAINING 6-O-PALMITOYL-D-GLUCOSAMINE)

The above liposome dispersion was prepared following the same procedures as in Example 9 except that 6-O-palmitoyl-D-glucosamine was used in place of 6-O-palmitoyl-D-glucosamine methylglycoside.

TEST EXAMPLES

The test examples performed to check the effects of the present invention will be described below. Note that the abbreviations to be used below have the following meanings.

Pc : Phosphatidylcholine
Chol : Cholesterol
Glu : 6-O-palmitoyl-D-glucosamine methylglycoside

TEST EXAMPLE 1 (MEASUREMENT OF ENCAPSULATION RATIO)

Method: In Example 9, the encapsulation ratio of the used SOD into the liposomes was obtained as follows. That is, the SOD activity in the supernatant liquid obtained after the centrifugal separation was determined by a nitrous acid method to obtain an amount of SOD not encapsulated into the liposomes. The obtained SOD amount was compared with the total amount of SOD initially added upon preparation of liposomes, thereby obtaining the encapsulation ratio of the SOD into the liposomes.

For the purpose of comparison, a neutral liposome dispersion consisting of Pc : Chol=8 : 2 (molar ratio) was prepared following the same procedures as in the above example without using any glucosamine derivative. The SOD encapsulation ratio of this dispersion was obtained following the same procedures as described above.

Results: The obtained results are summarized in Table-1 below.

TABLE 1

| Composition of membrane material | Encapsulation ratio (%) |
|---|---|
| Pc:Chol:Glu = 7:2:1 | 40.6 |
| Pc:Chol = 8:2 | 3.2 |

As is apparent from the above results, the cationic liposome containing the glucosamine derivative had a higher drug encapsulation ratio than that of the neutral liposome not containing the glucosamine derivative.

TEST EXAMPLE 2 (INTRACORPOREAL PHARNACOKINETICS)

Method: 500 μl of a $^3$H-labelled liposome dispersion prepared following the same procedures as in Example 9 were venously injected into the femoral vein of a ddy-type male rat put under anesthesia using urethane. The blood of the rat was sampled from its carotidartery into an Eppendorf tube at time intervals. The sampled blood was subjected to centrifugal separation, and the obtained supernatant liquid was poured into a vial of 100 μl. 700 μl of SOLUENE 350 were added and dissolved, and the resultant solution was neutralized by 180 μl of 2-N hydrochloric acid. After 6 ml of CLEAR-SOL were added, the radioactivity was measured using a liquid scintillation counter (LS 5000TA BECKMAN).

As a control, a $^3$H-labelled liposome dispersion consisting of Pc : Chol=3 : 1 (molar ratio) was prepared without using the glucosamine derivative of the present invention, and the radioactivity of the dispersion was measured following the same procedures as described above.

In addition, on the basis of the above results, the concentration in blood (μg/ml), the area under time curve (AUC: concentration in blood×time (hr)), and the halftime period in blood ($t_\frac{1}{2}$: hr) of each dispersion were calculated.

Note that the $^3$H-labelled liposome preparation used in this test was prepared following the same procedures as in Example 9 by adding a small amount (1/500,000 mol) of $^3$H-labelled dipalmitoylphosphatidylcholine upon mixing of membrane constituent.

Results: The obtained results are summarized in Table-2 below.

TABLE 2

| | Concentration in blood (μg/ml) | |
|---|---|---|
| time | Cationic liposome Pc:Chol:Glu = 7:2:1 | Neutral liposome Pc:Chol = 3:1 |
| 3 min | 13.762 ± 1.386 | 10.029 ± 1.592 |
| 10 min | 12.068 ± 0.852 | 8.648 ± 0.631 |
| 30 min | 11.256 ± 0.806 | 6.614 ± 0.591 |
| 1 hr | 10.408 ± 0.783 | 5.514 ± 0.241 |
| 2 hr | 9.461 ± 0.721 | 4.093 ± 0.158 |
| 4 hr | 7.598 ± 0.091 | 2.611 ± 0.453 |
| 6 hr | 6.625 ± 0.153 | 1.706 ± 0.348 |
| 8 hr | 5.660 ± 0.266 | 1.170 ± 0.302 |
| AUC | 123.92 μg × hr/ml | 30.27 μg × hr/ml |
| $t_\frac{1}{2}$ | 7.46 hr | 3.06 hr |

As is apparent from the above results, the AUC and the $t_\frac{1}{2}$ of the liposome of the present invention containing glucosamine derivative [I] as a membrane constituent were increased to about 4.1 times and about 2.5 times, respectively, compared with liposomes not containing the glucosamine derivative.

TEST EXAMPLE 3 (INTERORGAN DISTRIBUTION)

Method: Following the same procedures as in Test Example 2, $^3$H-labelled cationic liposomes were venously injected into the femoral vein of a rat put under anesthesia by urethane. After eight hours, the blood of the rat was entirely sampled, and its organs were delivered therefrom. The radioactivity was measured for the sampled blood and each of the delivered organs by using a liquid scintillation counter, thereby checking a liposome distribution state in each organ.

Results: The obtained results are summarized in Table-3 below.

TABLE 3

| | Cationic liposome PC:Chol:Glu = 7:2:1 | | Neutral liposome PC:Chol = 3:1 | |
|---|---|---|---|---|
| Organs | g | % | g | % |
| Liver | 2.0 | 13.0 | 3.2 | 24.5 |
| Spleen | 22.2 | 8.1 | 23.2 | 9.5 |
| Intestine | 0.2 | 3.7 | 0.6 | 9.0 |
| Lung | 0.3 | 0.4 | 0.5 | 0.5 |

TABLE 3-continued

| | Cationic liposome PC:Chol:Glu = 7:2:1 | | Neutral liposome PC:Chol = 3:1 | |
|---|---|---|---|---|
| Organs | g | % | g | % |
| Heart | 0.2 | 0.2 | 0.4 | 0.3 |
| Kidney | 0.4 | 0.7 | 0.5 | 0.8 |
| Lymph nodes | 0.2 | 0.0 | 0.5 | 0.0 |
| Muscle | 0.1 | — | 0.2 | — |

(n = 3)

As is apparent from the above results, the transmigration amount of the cationic liposomes of the present invention containing glucosamine derivative [I] as a membrane constituent to each organ was smaller than that of neutral liposomes not containing the glucosamine derivative. This reveals that the liposome of the present invention remains at a high concentration in blood and therefore circulates in a living body at a higher concentration. Therefore, the liposome of the present invention is excellent in blood-targeting properties.

TEST EXAMPLE 4 (ACUTE TOXICITY; NO. 1)

Novel glucosamine derivative [I] according to the present invention was used to perform a lethal toxicity test with respect to mice. The following compounds were used as to-be-tested substances.

① 6-O-palmitoyl-D-glucosamine methylglycoside
② 6,6'-di-O-palmitoyl-D-glucosamino-(→4)-β-D-glucosamine methylglycoside
③ Stearylamine (Comparative Example)

Each of the above compounds was suspended in a 0.5%-CMC·Na solution to prepare a to-be-tested solution. 1.0 ml of each to-be-tested solution was administered intraperitoneally to a 5-week-old ICR male mouse, and a mouse mortality state was observed. Note that 1.0 ml of a 0.5%-CMC·Na solution was similarly administered to a solvent control group.

The obtained results are summarized in Table-4 below.

TABLE 4

| Substance to be tested | Administered amount ng/kg | Number of dead individuals | | | | Total Number |
|---|---|---|---|---|---|---|
| | | Day of test | 1st day | 2nd day | 3rd day | |
| Control solvent | 0 | 0/5 | 0/5 | 0/5 | 0/5 | 0/5 |
| ① | 450 | 0/2 | 0/2 | 0/2 | 0/2 | 0/2 |
| | 900 | 0/2 | 0/2 | 0/2 | 0/2 | 0/2 |
| ② | 450 | 0/1 | 0/1 | 0/1 | 0/1 | 0/1 |
| | 900 | 0/1 | 0/1 | 0/1 | 0/1 | 0/1 |
| ③ | 250 | 0/5 | 0/5 | 0/5 | 1/5 | 1/5 |
| | 500 | 0/5 | 0/5 | 3/5 | 0/2 | 3/5 |
| | 1,500 | 0/4 | 0/4 | 1/4 | 3/3 | 4/4 |

As shown in Table-5 above, no dead individual was found during the observation period for compounds ① and ②. In addition, no significant change was found in a general condition after the administration, and an increase in weight was found as in the control. In contrast to this, for compound ③ as the Comparative Example, a decrease in spontaneous motion was found immediately after the administration, and the weight was gradually decreased to result in death.

These results reveal that novel glucosamine derivative [I] of the present invention has a significantly low toxicity and high safety as compared with stearylamine of the Comparative Example.

TEST EXAMPLE 5 (ACUTE TOXICITY; NO. 2)

The object of this test is to confirm a degree of toxicity of the cationic liposome of the present invention containing glucosamine derivative [I] in comparison to a conventional cationic liposome containing stearylamine in its membrane. For this purpose, a lethal toxicity test with respect to mice was performed for the liposome of the present invention and the conventional liposome each prepared without encapsulating a drug therein.

1. Preparation of To-Be-Tested Solution (1) Liposome Dispersion of the Present Invention Containing 6-O-Palmitoyl-D-Glucosamine Methylglycoside A liposome dispersion containing 6-O-palmitoyl-D-glucosaminemethylglycoside as a membrane constituent was prepared following the same procedures as in Example 9 except that no SOD solution was added. The prepared dispersion was condensed by using an ultrafiltration membrane and diluted with sterilized distilled water for injection as needed to obtain a to-be-tested solution.

(2) Conventional Liposome Dispersion Containing Stearylamine

A liposome dispersion containing stearylamine as a membrane constituent was prepared following the same procedures as for the above liposome dispersion of the present invention except that stearylamine was used in place of 6-O-palmitoyl-D-glucosamine methylglycoside. The prepared dispersion was condensed by an ultrafiltration membrane and diluted with injection sterilized distilled water as needed to obtain a to-be-tested solution.

Phosphorus content in the above to-be-tested solution was quantitatively analyzed by the ammonium molybdate method, and the concentration of 6-O-palmitoyl-D-glucosamine methylglycoside was calculated on the basis of the analysis value and the mixing ratio of phosphatidylcholine.

2. Test Method

Quarantined 5-week-old ICR male mice were divided into groups each consisting of two or three mice, and 2.0 ml of the above to-be-tested solution were administered intraperitoneally to each mouse once. On the other hand, 2.0 ml of sterilized distilled water were administered to mice of a solvent control group.

After the administration of the to-be-tested solution, the general condition was carefully observed at least once a day over 16 days to record toxicity symptoms and a mortality state.

3. Test Results

The obtained results are summarized in Table-5 below. Note that in Table-5, the meanings of symbols in the column of "substance to be tested" are as follows.

TABLE 5

① Liposome dispersion containing 6-O-palmitoyl-D-glucosamine methylglycoside
② Liposome dispersion containing stearylamine

| Substance to be tested | Administered amount* mg/kg | Number of dead individuals | | | Total number to 15th day |
|---|---|---|---|---|---|
| | | Day of test | 1st day | Days from 2nd day | |
| ① | 74.2 | 0/3 | 0/3 | 0/3 | 0/3 |
| | 369.8 | 0/3 | 0/3 | 0/3 | 0/3 |
| | 739.6 | 0/3 | 0/3 | 0/3 | 0/3 |
| | 1,154.8 | 0/3 | 0/3 | 0/3 | 0/3 |
| ② | 83.7 | 0/2 | 0/2 | 0/2 | 0/2 |
| | 146.0 | 0/2 | 0/2 | 0/2 | 0/2 |
| | 170.8 | 0/2 | 2/2 | — | 2/2 |
| | 340.0 | 0/2 | 2/2 | — | 2/2 |
| Solvent control | (2.0 ml) | 0/3 | 0/3 | 0/3 | 0/3 |

*Dosage indicated by the amount of 6-O-palmitoyl-D-glucosamine methylglycoside or stearylamine.

As shown in the above test rsults, no dead individual was found in the observation perid of the cationic liposome dispersion according to the present invention containing 6-O-palmitoyl-D-glucosamine methylglycoside. The $LD_{50}$ value of the dispersion as the amount of 6-O-palmitoyl-D-glucosamine methylglycoside is estimated to be 1,154.8 mg/kg or more.

On the other hand, dead individuals were found even with a low administered amount according to the conventional cationic liposome dispersion containing stearylamine as a membrane constituent. The $LD_{50}$ value of this conventional dispersion is estimated to be about 157.9 mg/kg (146.0 to 170.8 mg/kg).

As is apparent from the above test results, the cationic liposome of the present invention has a very low toxicity and is highly safe as compared with the conventional cationic liposome.

As has been described above in detail, novel glucosamine derivative [I] of the present invention is suitably used in the preparation of cationic liposomes. That is, the cationic liposome of the present invention prepared using this glucosamine derivative [I] is very low in toxicity in comparison to a conventional cationic liposome containing stearylamine as a membrane constituent. In addition, the cationic liposome of the present invention has a higher encapsulation ratio of anionic or neutral drugs than that of a conventional neutral or anionic liposome. Furthermore, the cationic liposome of the present invention has a long half-time period in blood and insignificant transmigration properties to organs.

In consideration of the above characteristics, the liposome preparation of the present invention is assumed to be widely applied to a physiologically active substance such as an SOD or medical drugs such as an anti-inflammatory drug, a hormone drug, and an anti-cancer drug. In particular, the liposome preparation of the present invention encapsulating the SOD is assumed to be effective to various diseases (e.g., therapies for a chronic inflammatory disease, cardiopathy and encephalopathy caused by an ischemia-reperfusion injury, and a digestive organ disease).

We claim:

1. A glucosamine derivative represented by the following formula (I) or a pharmacologically acceptable salt thereof:

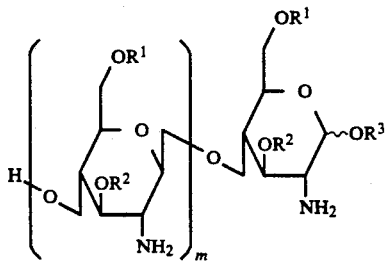

wherein $R^1$, $R^2$, $R^3$, and m represent the following
$R^1$ and $R^2$;
  a hydrogen atom or a —CO(CH$_2$)$_n$CH$_3$ group, n representing an integer from 10 to 22 and $R^1$ and $R^2$ being not simultaneously hydrogen atoms
$R^3$;
  an alkyl group having 1 to 4 carbon atoms and
m;
  an integer from 0 to 3.

2. A compound according to claim 1, wherein said glucosamine derivative represented by formula is selected from the group consisting of
  6-O-lauroyl-D-glucosamine methylglycoside
  6-O-myristoyl-D-glucosamine methylglycoside
  6-O-palmitoyl-D-glucosamine methylglycoside
  6-O-stearoyl-D-glucosamine methylglycoside
  3,6-di-O-lauroyl-D-glucosamine methylglycoside
  3,6 di-O-myristoyl-D-glucosamine methylglycoside
  3,6-di-O-stearoyl-D-glucosamine methylglycoside, and
  6,6'-di-O-palmitoyl-D-glucosamino-(1→4)-β-D-glucosamine methylglycoside.

3. A liposome containing a glucosamine derivative according to claim 1 or a pharmacologically acceptable salt thereof as a membrane constituent.

4. A liposome according to claim 3, containing, as a membrane constituent, 0.5 to 30 parts by weight of said glucosamine derivative with respect to 100 parts by weight of a phospholipid.

5. A liposome according to claim 3 or 4, containing a sterol-based stabilizer and/or an antioxidant as other membrane constituents.

6. A liposome according to claim 3, encapsulating a pharmacologically or physiologically active substance in a vesicle.

7. A liposome according to claim 6, wherein said pharmacologically or physiologically active substance is electrically neutral or anionic.

8. A liposome according to claim 7, wherein said pharmacologically or physiologically active substance is selected from the group consisting of
  an anti-inflammatory drug, an oxygen carrier, an enzyme drug, an antibiotic, a hormone drug, and an anticancer drug.

9. A liposome according to claim 8, wherein said pharmacologically or physiologically active substance is a superoxide disproportionation enzyme.

* * * * *